(12) United States Patent
Robertson et al.

(10) Patent No.: US 7,204,978 B1
(45) Date of Patent: Apr. 17, 2007

(54) TREATMENT AND DIAGNOSIS OF INFERTILITY USING TGFβ OR ACTIVIN

(75) Inventors: Sarah Anne Robertson, St. Peters (AU); Kelton Paul Tremellen, Vale Park (AU)

(73) Assignee: The University of Adelaide, Adelaide, South Australia (AU)

( * ) Notice: Subject to any disclaimer, the term of this patent is extended or adjusted under 35 U.S.C. 154(b) by 0 days.

(21) Appl. No.: 09/380,327

(22) PCT Filed: Mar. 6, 1998

(86) PCT No.: PCT/AU98/00149

§ 371 (c)(1),
(2), (4) Date: Sep. 3, 1999

(87) PCT Pub. No.: WO98/39021

PCT Pub. Date: Sep. 11, 1998

(30) Foreign Application Priority Data

Mar. 6, 1997 (AU) .................................... P05508

(51) Int. Cl.
*A61K 39/00* (2006.01)
*A61K 45/00* (2006.01)
*A61K 35/24* (2006.01)
*A61K 35/52* (2006.01)

(52) U.S. Cl. .................. 424/85.1; 424/184.1; 424/537; 424/561

(58) Field of Classification Search ................ 424/85.1, 424/184.1, 537, 561; 435/806; 436/906
See application file for complete search history.

(56) References Cited

U.S. PATENT DOCUMENTS 5,166,190 A 11/1992 Mather et al.
5,395,825 A * 3/1995 Feinberg et al.

FOREIGN PATENT DOCUMENTS

WO   WO 91/10445   7/1991
WO   WO 95/04931   2/1995

OTHER PUBLICATIONS

Chaouat G, Immunologic Consequences of vaccination against abortion in mice, Mar. 1985, J. Ummunol 134(3): 1594-8.*
Toder V, Mouse Model for the Treatment of Immune Pregnancy Los, 1991, American J. Reproductive Immunol 26: 42-46.*
Dunker et al, Targeted mutations of transforming growth factor-beta genes reveal important roles in mouse development and adult homeostasis, Dec. 2000, Eur J Biochem 267(24): 6982-8.*
Ngo et al, in The Protein Folding Problem and Tertiary Structure Prediction, 1994, Merz, et al., (ed.), Birkhauser, Boston, MA, pp. 433 and 492-495).*
Clark et ak, Hum Reprod 9(12): 2270-7, Dec. 1994.*
Lyons et al, J Cell Biol 110(4): 1361-7, Apr. 1990.*
Harlow et al, in A Laboratory Manual, Cold Spring Harbor Laboratory, p. 61, 1988.*
Tuan et al, Connect Tissue Res 34(1): 1-9, 1996.*
Grainger et al, Nat Med 1(9):932-7; Sep. 1995.*
Anonymous, in World Health Organization Laboratory Manual for the Examination of Human Semen and Semen Cervical Mucus Interaction, Cambridge University Press, NY, pp. 3-11, 1987.*
Heidenreich et al, Am J. Reprod Immunol 31(2-3):69-76, Mar.-Apr. 1994.*
Martin-Villa et al, Biol Reprod 55(3): 620-9, Sep. 1996.*
Ober et al, The Lancet 354: 365-369, Jul. 1999.*
Coulam et al, Am J. Reproduc Immunology 32: 55-72, 1994.*
Pearson et al, Nature 420: 265-266, Nov. 2002.*
Lea et al, Am J. Reprod Immunol 34(1): 52-64, Jul. 1995.*
Nocera et al, Am J. Reprod. Immunology 33: 282-291, 1995.*
Thomas et al, Am J Reprod. Immunol 6(4): 185-9, Dec. 1984.*
Thaler et al, Am J Reprod Immunol 21(3-4): 147-50, Nov.-Dec. 1989.*
Prakash et al, Reproductive Immunology 70: 403-412, 1981.*
Grainger et al, Nat Mad 1(9): 932-7, Sep. 1995.*
Heidenreich et al, Am J Reprod Immunol 31(2-3): 69-76, Mar.-Apr. 1994.*
Tremellen et al 2002, www.usnews.com articles 021021.*
Robertson 2002, www.adelaide.edu.au/robertsons.*
Michel et al.1990 Br.J. Obstet.Gynaecol, V.97, pp. 084-988.*
Graham et al., 1994, Exp.Cell Res. V.214, pp. 93-99.*
Graham et al., 1992 Biochem Cell Biol. vol. 70, pp. 867-874.*
"Suppressed Cell-Mediated Immunity and Monocyte and Natural Killer Cell Activity Following Allogeneic Immunization of Women with Spontaneous Recurrent Abortion"; Grafter et al., *Journal of clinical Immunology*, 17(5)m 408-419; 1997.
"Characterization of Latent Transforming Growth Factor-β From Human Seminal Plasma" Nocera et al., *American Journal of Reproductive Immunology* 33, 282-291, 1995.
"Localization of seminal plasma transforming growth factor-β1 on human spermatozoa: and immunocytochemical study" Chu et al., *Fertility and Sterility* 66(2), 327-330, 1996.
Clark et al., "Murine Pregnancy Decidua Produces a Unique Immunosuppressive Molecule Related to Transforming Growth Factor β-2$^1$", The Journal of Immunology, vol. 144, 3008-3014, No. 8, Apr. 15, 1990.

(Continued)

*Primary Examiner*—Christina Chan
*Assistant Examiner*—Michail A. Belyavaskyi
(74) *Attorney, Agent, or Firm*—Proskauer Rose LLP

(57) ABSTRACT

A method of treating an infertility condition in humans or mammals, by exposure of a prospective mother to TGF beta or derivative or analog of TGF beta. The exposure is advantageously in conjunction with one more antigens of a prospective father so that a hyporesponsive immune reaction is mounted to the one or more antigens of the prospective father.

27 Claims, 6 Drawing Sheets

OTHER PUBLICATIONS

Immunity's Pregnant Pause, Nature, Nov. 21, 2002, pp. 265-266, vol. 420.

Gentle Persuasion, New Scientist, Feb. 9, 2002, pp. 32-35.

Anie Philip et al., "Interaction of Transforming Growth Factor-β1 with α$_2$-Macroglobulin", The Journal of Biological Chemistry, Nov. 25, 1991, pp. 22290-22296, vol. 266, No. 33.

Laiage M. Wakefield et al., "Recombinant Latent Transforming Growth Factor β1 Has a Longer Plasma Half-Life in Rats than Active Transforming Growth Factor β1, and a Different Tissue Distribution", The Journal of Clinical Investigation, Inc., Dec. 1990, pp. 176-1984, vol. 86.

The Australian Society for Medical Research, South Australian Division, Scientific Meeting, May. 31st, 1996, Abstracts.

Robertson et al., "Granulocyte macrophage colony stimulating factor (GM-CSF) in the murine reproductive tract: stimulation by seminal factors", Reprod. Fertil. Dev., (1990), 2(4):359-68 (Abstract).

Robertson et al., "Role of high molecular weight seminal vesicle proteins in eliciting the uterine inflammatory response to semen in mice", Journal of Reproduction and Fertility (1996), 107, 265-277.

The Australian Society for Medical Research, 35th National Scientific Conference, Nov. 24-27, 1996, Program and Abstracts.

* cited by examiner

US 7,204,978 B1

TREATMENT AND DIAGNOSIS OF INFERTILITY USING TGFβ OR ACTIVIN

This application is a §371 of PCT/AU98/00149 (WO 98/39021), filed Mar. 6, 1998.

FIELD OF THE INVENTION

This invention relates to a diagnostic method for an infertility condition giving rise to reduced ability to have offspring and to a method of treating such a condition.

BACKGROUND OF THE INVENTION

An inability or reduced ability to have children can cause great personal distress and has a high attendant social cost, particularly in terms of the cost of medical intervention. A large proportion of couples fall into this category. In the USA, for example, it is said that some 10–15% of couples of reproductive age are unable to have children, whereas in the United Kingdom this is 14%. In 1995 it was calculated that 5.1 million women had impaired fertility in the USA alone, with this figure projected to increase to 5.9 million by the year 2020 (56). In the US, the cost of a pregnancy conceived by IVF varies between US$66,000 for the first cycle to US$114,000 by the sixth cycle (60).

In the context of this specification an infertility condition is to be understood to relate not only the capacity to conceive but also the miscarriage, spontaneous abortion or other pregnancy-related conditions, such as pre-eclampsia, and includes sub-fertility.

Recent studies have revealed that a major proportion of interfile couples are childless because of a higher than normal rate of early embryonic loss (70% miscarriage v 21% miscarriage in fertile controls: 57), rather than an inability to conceive. These findings have initiated a search for reasons for the increased rate of early embryonic loss in infertile couples, as well as potential therapies to avert such losses.

In the last 20 years or so some hope has been held out to infertile couple with the development of in vitro fertilisation (IVF) techniques. These IVF techniques generally take the form of stimulating the female to ovulate, contacting collected ova with sperm in vitro and introducing fertilised ova into the uterus. Multiple variations of this general process also exist. Despite considerable research and technical advances in the IVF field the rate of successful pregnancy following IVF treatment is still quite low and is in the order of 15 to 25% per cycle.

Undertaking an IVF program often causes great anguish, especially when there is no resultant successful pregnancy. It is presently believed that the poor success rate in IVF treatment is due to an extraordinarily high rate of early embryonic loss (58, 59), possibly related to the patient's impaired reproductive state or the IVF process itself.

The low efficacy of IVF, together with its high cost and the associated psychological trauma from repeated treatment failures makes it desirable that alternative approaches to the problem of infertility are sought. Current methods of increasing pregnancy rates during IVF treatment include placing multiple embryos (2–5) into the uterine cavity, but this is not always effective since uterine receptivity is believed to be at fault at least as commonly as embryonic viability. Furthermore, the ensuing high rates of multiple pregnancy are associated with an increased material risk of pre-eclampsia, haemorrhage and operative delivery, and fetal risks including pre-term delivery with the attendant possibility of physical and mental handicap.

Similarly, early pregnancy loss is a major constraint in breeding programs for livestock and rare or threatened species. Embryonic mortality during the pre- and per-implantation period is viewed as the major reason for poor pregnancy outcome when assisted reproductive technologies such as artificial insemination are used. Even following natural mating, variability in litter size and in the viability of offspring are additional limitations with serious economic implications.

The reasons for increased rates of early embryonic loss following natural and assisted conception remain unknown. Chromosomal studies on miscarried embryos have confirmed that at least half of these embryos are genetically normal (61). Normal embryos appear to be lost primarily because the environment provided by the material tract during pre-implantation development or at the time of implantation into the endometrium is insufficient to nurture their growth and development. Embryos may lose viability or developmental potential if the material tract milieu comprises inappropriate or insufficient nutrients or peptide growth factors. Moreover, a primary determinant of uterine receptivity is provided by the maternal immune response to the conceptus, which is perceived as foreign or semi-allogeneic due to expression of both maternal and paternal antigens.

Medawar originally hypothesised that maternal immune accommodation of the semi-allogeneic conceptus may be facilitated by immunological tolerance to paternal transplantation antigens (major histocompatibility [MHC] antigens) (70). This hypothesis lost favour when it was found that pregnancy does not permanently alter the capacity of mice to reject paternal skin grafts (5, 46). However, the concept of transient hyporesponsive to paternal MHC antigens (46) is now receiving renewed attention, as a recent study by Tafuri et al (31) has provided clear evidence to show that during murine pregnancy, T-lymphocytes reactive with paternal class 1 MHC become 'anergic', or unable to recognise antigen due to internalisation of T-cell receptors. This anergic state conferred 'tolerance' to paternal MHC antigen-expressing tumor cells, and was functionally operative from as early as implantation (day 4 of pregnancy) and lasted until shortly after parturition when lymphocytes regained their reactivity. The data support the hypothesis that a permissive maternal immune response to other antigens expressed on the embryo, or the fetal-placental unit (hereinafter referred to as the conceptus) may similarly be due to induction of a tolerant immune response specific to those antigens.

Just precisely what is responsible for inducing this tolerance of paternal MHC antigens and other conceptus antigens has heretofore been unclear. Additionally the nature of the tolerance was unclear.

The term tolerance in the context of this invention is taken to mean inhibition of the potentially destructive cell-mediated immune response against conceptus antigens, and/or inhibition of synthesis of conceptus antigen-reactive immunoglobulin of complement-fixing isotypes (for example the 'Th1' compartment of the immune response). This tolerance may or may not be associated with induction of synthesis of non-destructive, conceptus antigen-reactive immunoglobulin of the non-complement-fixing isotypes and subclasses (for example the 'Th2' compartment of the immune response). The term tolerance should be taken to encompass T cell energy and other permanent or transient form of hypo-responsiveness or suppression of the maternal Th1 compartment.

Tafuri et al (31) have shown that paternal antigen-specific tolerance is active by the onset of blastocyst implantation on day 4 of pregnancy in mice. The pre-implantation embryo is a poor antigenic stimulus since it usually comprises fewer than 100 cells and is enveloped by a protective coat (zona pellucidé) until just before implantation. Semen however is richly endowed with paternal antigens present on and within sperm, somatic cells and the seminal plasma itself, and comprises an effective priming inoculum for many paternal antigens (5) known to be shared by the conceptus. Up until now seminal plasma has been conventionally thought to function primarily as a transport and survival medium for spermatozoa traversing the female reproductive tract (21). The recent studies described by the inventors in this specification have highlighted a hitherto unappreciated role for this fluid in interacting with maternal cells to induce a cascade of cellular and molecular events which ultimately lead to maternal immune tolerance to paternal antigens present in semen and shared by the conceptus, thereby abrogating immune rejection during implantation.

Ejaculation during coitus provokes a leukocyte infiltrate as the site of semen deposition termed the 'leukocytic cell reaction' in a variety of mammalian species, including man (1). In mice, the cascade of cellular and molecular changes initiated by the introduction of semen into the uterus, in many respects, resembles a classic inflammatory response. Within hours after mating, a striking influx and activation of macrophages, neutrophils, and eosinophils occurs in the endometrial stroma (2–4), in association with upregulated expression of major histocompatibility complex (MHC) class II and CD86 antigens by endometrial dendritic cells, followed by enlargement of draining lymph nodes (5,6). This inflammatory response is transient and fully dissipates by the time of embryo implantation on day 4 of pregnancy (2–4), when leukocytes persisting in the endometrium are predominantly macrophages with an immunosuppressive phenotype (7).

The temporal changes in trafficking and phenotypic behavior of endometrial leukocytes during the period between mating and implantation are likely to be orchestrated principally by cytokines emanating from steroid hormone regulated epithelial cells lining the endometrial surface and comprising the endometrial glands (8). Of particular importance are granulocyte-macrophage colony-stimulating factor (GM-CSF) and interleukin-(IL-)-6, the synthesis of which is upregulated at least 20-fold and 200-fold respectively in estrogen primed epithelial cells following induction by specific proteinaceous factors in seminal plasma (8.9) known to be derived from the seminal vesicle gland (10). Previous studies have implicated the surge in epithelial GM-CSF release as a key mediator in the post-mating inflammatory response since injection of recombinant GM-CSF into the estrous uterus is sufficient to produce cellular changes resembling those seen following natural mating (11). The inventors have found, using GM-CSF deficient mice, that the chemotactic activity of GM-CSF is likely to be compensated or augmented by an array of chemokines, the expression of which is transiently upregulated after mating (12), and cytokines synthesised by activated endometrial macrophage including IL-1 and tumour necrosis factor-α (TNF-α)(4).

The present inventors have investigated the nature of the seminal factor which acts to stimulate GM-CSF release from the uterine epithelium. Previous experiments have shown that the increase in uterine GM-CSF content is neither the result of introduction of GM-CSF contained within the ejaculation, nor a consequence of a neuroendocrine response to cervical stimulation, and is independent both of the presence of sperm in the ejaculation and MHC disparity between the male and female (8). A mechanism involving induction of GM-CSF mRNA synthesis in epithelial cells by proteinaceous factors derived from the seminal vesicle was suggested by experiments showing that seminal vesicle-deficient (SV−) males did not evoke GM-CSF release or a post-mating inflammation-like response in females, and that trypsin-sensitive, high molecular weight material extracted from the seminal vesicle could upregulate GM-CSF release from uterine epithelial cells in vivo (10).

It has, however, not been clear from previously published work that this inflammatory response is related to the induction of tolerance by the mother to the conceptus, or alternatively whether the inflammatory response has a role in enhancing the immune system to combat the influx of foreign matter such as potential pathogenic bacteria is not clear. Nor is there any indication as to what the trigger for the induction of tolerance is or indeed that tolerance is mediated by semen.

One known relevant prior art document is U.S. Pat. No. 5,395,825 by Feinberg. This specification discloses a finding that suggests that elevated TGFβ in the female reproductive tract can facilitate production of fibronectin, a protein hypothesised to assist implantation by promoting adhesion of the embryo to the endometrial surface. The half life TGFβ is only a few minutes and its effect on fibronectin is very short term. Therefore the administration of TGFβ in the above method can only be contemplated to assist implantation is delivered at precisely the time at which the pre-implantation embryo arrives in the uterine cavity. The present invention does not require such temporal precision in TGFβ delivery, nor does it purport that the effect of TGFβ is mediated through fibronectin.

SUMMARY OF THE INVENTION

The inventors have identified TGF-β as a principal immune regulatory molecule within seminal plasma. TGFβ produced in the latent form in the seminal vesicle gland is activated within the female reproductive tract where is acts to induce GM-CSF synthesis in uterine epithelial cells, thereby initiating the post-coital inflammatory response.

Additionally the inventors have shown that TGFβ, when administered to the female reproductive tract together with sperm or semen, can elicit tolerance towards male antigens, including paternal MHC class I antigens. This state of tolerance is evidenced by inhibition of Th1-type immune responses to paternal antigens, including delayed-type hypersensitivity (DTH) responses primed by a previous injection with sperm, production of complement-fixing isotypes of immunoglobulin specific for sperm, and cell-mediated immune rejection of tumor cells bearing the same MHC class I antigens as contained in the priming sperm inoculum. It is proposed that this tolerance might be achieved by exposure of the female to TGFβ either with or without male antigen. The significance of this is that it is highly likely that certain infertility conditions will be related to the incapacity to produce tolerance to antigens of the male and/or to provide a suitable cytokine environment for growth and development of the pre-implantation embryo, as a result of either a lack of TGFβ in the seminal fluid of the male, an incapacity of the female to process the TGFβ from an inactive to an active form, or an absence or low levels of paternal antigens in the ejaculate. In some instances infertility may be due to the inability of the female to respond to TGFβ, in which case direct application of molecules induced by TGFβ, such as GM-CSF, may be warranted.

The TGF-β1 content of murine seminal vesicle secretions, like that of human seminal plasma (22), was found to be extraordinarily high and second only to that reported for platelet distillate (23). In mammalian species the TGF-β family comprises at least three closely related polypeptides, TGF-$β_1$, -$β_2$ and -$β_3$ (24), which exhibit 70–80% sequence homology and share many biological actions. TGFβ$_1$ is the dominant TGFβ isotype responsible for increasing murine uterine GM-CSF output, since TGFβ$_1$-specific neutralising antibody is now found to have the ability to block 85% of seminal vesicle GM-CSF stimulating activity (FIG. 2). Other members of the TGFβ superfamily, such as TGFβ$_2$ and activin, have also now been identified as capable of eliciting an increase in uterine GM-CSF output (FIG. 4). These additional members of the TGF-β family, complexed with other carrier proteins such as the 250–300 kDa binding protein betaglycan (25) may account for the higher molecular weight activity present in murine seminal vescile fluid and human seminal plasma (22).

The synthesis of TGFβ as a latent complex is believed to have a stabilising effect (26) and focus its activity at the target site by binding to extracellular matrix (27). Evidence for a uterine mechanism for activation of latent TGF-β was provided by the present finding that in contrast to activity in the seminal vesicle, the majority of the TGFβ$_1$ found in the uterine luminal fluid after mating was in the active form (FIG. 5). Plasmin or other proteolytic enzymes derived from uterine cells or the male accessory glands (28, 29, 47) may contribute to the activation of TGFβ after ejaculation.

The proposal that components of the ejaculate can indirectly contribute to pregnancy success is supported by experiments in accessory gland-deficient mice (36, 37) and the finding that poor pregnancy outcome and dysregulated fetal and/or placental growth after embryo transfer or during first pregnancy in various livestock species (38–40) can be partially ameliorated by prior exposure to semen (41, 42). Likewise, studies in humans now clearly identify lack of exposure to semen due to limited sexual experience, use of barrier methods of contraception, or in IVF pregnancies with increased risk of implantation failure, spontaneous abortion and pre-eclampsia (43–45).

In a broad form the invention could be said to reside in a method of treating an infertility condition in a human or mammal by exposure of the prospective mother to TGFβ or an effective derivative or analog thereof before attempted conception to elicit a transient hyporesponsive immune reaction to one or more antigens of a prospective father to thereby alleviate symptoms of the infertility condition.

In another broad form the invention could be said to reside in a method of treating an infertility condition in a human or mammal by exposure of a prospective mother to one or more antigens of a prospective father and to TGFβ or an effective derivative or analog thereof before attempted conception to elicit a transient hyporesponsive immune reaction to said one or more antigen to thereby alleviate symptoms of the infertility condition.

Preferably a mucosal surface of the prospective mother is exposed to the antigen, and more preferably the mucosal surface is the genital mucosal surface, however, it is feasible that exposure at other mucosal surfaces can give rise to the transient paternal antigen tolerance. There are two basic reasons that this might be the case, firstly it is known that tolerance to external antigens can be elicited at mucosal surfaces, thus it is known that women that are exposed to seminal fluid orally show evidence of reduced pre elampsia effects to MHC antigens of the male partner (48). Thus the exposure could be oral, respiratory, gastrointestinal or genital. For example the surface antigen and TGFβ may be presented as an oral or nasal spray, or as a rectal or vaginal gel. Such a gel might for example be a gel such as used in the vaginal gel sold under the brand name PROSTIN (Upjohn Pty Ltd). Alternatively it might be desired to take the TGFβ and the surface antigen in a form that gives exposure to the small and perhaps large intestines, such as perhaps contained in a gelatin capsule.

Whilst a mucosal exposure may be preferred because it is likely to give risk to a transient tolerant immune reaction, it may also be feasible to provide for another route of exposure. Thus the surface antigen and TGFβ may be injected for systemic contact.

It may be desirable to deliver the TGFβ and the antigen together, for example where the two are combined in a gel, or spray, alternatively, it might be desirable to provide a source of TGFβ at the mucosal surface of interest, which might be the genital tract, and the antigen could subsequently be deposited onto the mucosal surface. It is also not yet clear whether the TGFβ needs to be present at the same time as the antigen is present, although it is believed to be preferable, however, it is proposed that it may be possible to have a delay between the delivery of the TGFβ and the surface antigen. Thus an alternative would be to deposit the antigen first perhaps as an ejaculate and then deliver the TGFβ as a pessary after intercourse.

The nature of the relevant surface antigens is not entirely clear, but will presumably be those that are particularly antigenic and prominent either on the sperm, or on the conceptus. The most likely candidates are MHC antigens, and more preferably MHC class I. The most efficient manner of presenting these antigens is in the form that they are naturally present—on any appropriate cell of the intended male parent that expresses them and those cells would include sperm cells and may include leukocytes. The antigens may also be presented in biological fluids such as seminal plasma which is known to carry certain male antigens (49). This use of cells other than sperm cells will be pertinent where the sperm count of the prospective father is somewhat low. The use of cells other than sperm cells may be preferred where a non-genital route is used. Alternatively the antigens may be presented in purified or semi-purified form, which may or may not be presented on inert or adjuvant carriers, thus for example it may be presented in the carriers known as ISCOMS. This latter approach however is likely to be more technically complex and expensive. It is additionally possible that the antigens may be encoded within sperm cells in the form of mRNA (or other nucleic acid) and this RNA message is then expressed by maternal genital tract cells. It may be that TGFβ therefore plays a role in promoting the events leading to presentation of paternal antigen to maternal lymphocytes through activating genital tract antigen presenting cells to take up and translate sperm mRNA.

The level of TGFβ may be varied, and will vary depending upon which species is being treated. For humans the level of TGFβ will preferably be greater than 50 ng/ml with a total dose of 150 ng/ml and more preferably at a concentration of between 100 and 400 ng/ml with a total dose of between 100 to 200 ng. The level of TGFβ in normal male semen is in the order of 200 ng/ml. This level can be judged empirically when assessing other animals, and thus for horses or cattle the preferred level is expected to be in the order of 100 ng/ml. These levels may vary if the TGFβ is supplied in a slow release depot, perhaps as a patch or as a gel or latent TGFβ complex.

The level of exposure to surface antigens may vary, in a preferred form the exposure will be to the prospective mother's genital tract in the form of the prospective father's ejaculate, and the level of exposure will be determined by the cell count and antigenic density on the surface of such cells. Where cells are administered other than in the above manner, a similar number of cells might be used, however, the most effective manner may be determined empirically. It is thought that an exposure of leukocytes in the order of $10^7$–$10^9$ cells might be the appropriate level of exposure to a mucosal surface.

This specificity of TGFβ to be co-administered with the male antigens is at present not entirely clear, and because TGFβ$_1$ is thought to be responsible whereas TGFβ$_{2,3}$ are less important, it is more likely that TGFβ$_1$ is to be used. It will however also be understood that various modification might be made to TGFβ$_1$ or indeed TGFβ$_2$, or TGFβ$_3$ which could be effective in eliciting an effective transient tolerant immune reaction either separately or in combination with another agent. Such modified TGFβ's might include substitution, deletion or addition mutants, and might include peptide fragments, which may or may not be incorporated into another protein to make a recombinant protein. Alternatively other members to the TGFβ superfamily may also be used or used as a starting point to developing an analog to the TGFβ activity, one such member is known as activin.

Where unmodified TGFβ is used it will preferably be administered as TGFβ$_1$. The TGFβ$_1$ may be administered in its active form, however, where the prospective mother is capable of activating TGFβ$_1$ it may also be administered in its precursor form. An alternative "delivery" option would be natural TGFβ such as in the form of platelets. Thus instead of purified TGFβ a preparation of platelets or other source rich in natural TGFβ, such as milk or colostrum, may be used.

The exposure is preferably a multiple exposure. The multiple exposure is preferably performed over a period of at least three months, with the mucosal surface being exposed to TGFβ during each exposure to the prospective father's antigens. This period of time could however be somewhat reduced, and it may be possible to achieve improvement with one exposure but as a minimum it is anticipated that exposure would be at least one week before conception is attempted. It may also be preferred that non-barrier contraceptive measures be taken prior to the planned conception, where the antigens are associated with sperm cells and these are administered to the genital tract, so that there is some certainty of a period of exposure to the prospective father's antigens before conception. This is particularly the case where the fertility condition is of the type where conception takes place but either miscarriage, spontaneous abortion or pre-eclampsia occurs after conception.

It is also envisaged that the administration of TGFβ in the presence or absence of the at least one surface antigen may need to continue past the prospective date of conception perhaps for the first 12 weeks of pregnancy.

In an alternative form the invention could be said to reside in a method of diagnosing an infertility condition in males by testing the level of TGFβ in seminal fluid.

Greater than 70% of the TGF-β$_1$ in seminal vesicles exists in the latent form. The infertility condition might therefore not be due to a lack of TGFβ in the semen of the male partner but it may be that the female cannot process the inactive form of the TGFβ. The invention could therefore also be said to include the method of exposing inactive form of TGFβ to the genital tract of a female and testing for her capacity to convert the inactive form of TGFβ to active TGFβ. If this is found to be the case, the method of treating the fertility condition will include administration of active TGFβ, or alternatively a compound capable of activating TGFβ can be administered, such as plasmin, so as to increase the level of active TGFβ.

In a preferred form the method of treating infertility will first include the step or diagnosing or testing whether the male has adequate levels of TGFβ or the female has the capacity to activate TGFβ, or alternatively whether anti-sperm antibodies exist.

The use of the present invention may be used in conjunction with IVF treatment, whereby the transient tolerant immune response is elicited before transfer of the conceptus or gametes is attempted. It is expected however that where the infertility condition is caused as a result of reduced TGFβ level in semen, or capacity to activate TGFβ, it is likely that the trauma of IVF treatment may not be needed and that a 'natural' conception may be possible in its place.

It will be understood that this invention is not necessarily limited to humans, but may also extend to treatment of other mammals including livestock species.

Some specific disorders or procedures that may benefit from the present invention are now discussed to some degree.

Recurrent miscarriage. It is known that approximately 2–5% of couples are involuntarily childless due to recurrent miscarriage. The aetiology of recurrent miscarriage is complex, but in the vast majority of causes no chromosomal, hormonal nor anatomical defect can be found and an immunological lesion is implicated. A variety of therapies which attempt to modify the mother's immune response to the semi-allogeneic conceptus have been trialed with variable success. The predominant therapeutic approach over the past 20 years has been to inject women with paternal leucocytes in the hope of achieving 'tolerance' to paternal antigens. This therapy has had limited success with a meta-analysis of 15 trials concluding that paternal leucocyte immunisation can increase pregnancy rates by 8–10% (51).

Coulam % Stern (52) have administered seminal plasma from a pooled donor source to the genital tract of women with recurrent miscarriage and were able to produce a non-statistically significant increase in live birth rates (60% v 48%, p=0.29 n=86). This treatment differs significantly from a preferred therapeutic regime in that seminal plasma was administered in the absence of paternal antigen. It is not surprising that the success of this therapy was limited, since no paternal antigen was administered.

The data supporting the present invention provide encouraging results which indicate that TGFβ may be a beneficial treatment for recurrent miscarriage because of its potent immune modulating capacity. It is expected that administration of sperm in combination with TGFβ will help produce a tolerant or 'nurturing' immune response to a future conceptus which would share some of the same MHC class I or other antigens.

Adjunct to IVF treatment. It is currently believed that the premenstrual pregnancy wastage produces a significant negative contribution to IVF success rates. One theory for this increased early pregnancy loss is that IVF is an 'unnatural' process that separates the act of intercourse from conception. This would mean that IVF recipients may not be exposed to seminal plasma and it's associated antigens early in pregnancy. Several animal studies and human investigations, including the randomised control trial described herein, have suggested that exposure of the female genital tract to semen at the initiation of a pregnancy, as well as prior to a pregnancy, is beneficial to subsequent pregnancy outcome. It is proposed that there will be some benefit derived from giving women exogenous TGFβ in combination with partner's sperm/leucocytes at or near the time of embryo transfer, especially if the partner's seminal plasma TGFβ content is low or sperm numbers are low.

Anti-sperm antibody therapy. A significant proportion of infertility is due to the presence of anti-sperm antibodies in either the male or female partner (53). Seminal plasma has been shown to suppress the formation of anti-sperm antibodies in the female serum and genital tract secretions of the mouse. One of the active agents within seminal plasma responsible for suppressing maternal production of potentially damaging, complement-fixing isotypes or subclasses of immunoglobulin specific for sperm antigens has been identified as TGFβ. It is expected that the present invention may, in at least some instances, block anti-sperm antibody formation. The relationship between maternal anti-sperm antibody formation in women and their partner's seminal plasma TGFβ concentration will be investigated to confirm this. Current therapies for anti-sperm antibodies are not sufficiently effective (for example oral steroids or the prolonged use of barrier contraception) or require expensive assisted reproduction therapy. It is proposed that administration of a TGFβ-containing pessary following intercourse will abrogate this anti-sperm antibody response and enable natural pregnancy to ensure.

Pre-eclampsia and IUGR prophylaxis. Pre-eclampsia and some forms of intra-uterine growth restriction (IUGR) are believed to be an immunological disorder due to 'shallow' placentation resulting from a damaging. Th1-type immune attack on the invasive trophoblast. There is epidemiological evidence showing that repeated exposure of a women to her partner's antigens through intercourse in the absence of barrier contraception decreases her chances of developing pre-eclampsia in a subsequent pregnancy to that partner (54, 55). This may be brought about by the generation of maternal 'tolerance' towards paternal antigens as a consequence of repeated exposure at intercourse, which facilitates placental growth and invasion of the maternal decidua. Some women have a propensity to develop pre-eclampsia or to suffer fetal growth restriction every time they become pregnant. This may be due to inadequate TGFβ content of their partner's semen, or an ability to process latent TGFβ into a biologically active form.

Priming with partner's antigens in combination with TGFβ before conception and perhaps until 3 months of pregnancy, by which time placental invasion is complete, may help prevent the development of pre-eclampsia and IUGR in these high risk women.

Prospective analysis of stud animal fertility in livestock breeding industries. Variability in the productivity of stud males is a major constrain in pig, cattle, sheep and other livestock breeding programs. In many species there are substantial differences between studs, particularly in the pre-implantation mortality of embryos sired, even within a given hard. Currently, reliable estimation of the fertility and fecundity of a stud male is only possible after documentation of the outcome of multiple pregnancies. Measurement of the TGFβ content of seminal plasma of potential studs, for example by simple enzyme-linked immunsorbent assay, is likely to be an effective tool in livestock breeding management. Such measurements may need to be taken over the course of some weeks and could be made in conjunction with measurements of other factors known to inhibit the action of TGFβ, such as interferon-γ.

Optimisation of pregnancy outcome in livestock breeding industries. A primary determination of the productivity of livestock breeding programs, particularly in species such as the pig where litters are large, is variability in the litter size and weight of offspring. As detailed above, these parameters are believed to be influenced largely by the extent to which the mother's immune response is 'tolerated' to paternal antigens shared by the conceptus. Pregnancy outcome is often further compromised where the pregnancy is initiated by artificial insemination, particularly when artificial semen extenders, as opposed to seminal plasma, are employed as the carrier. Since the frequency of mating between breeding females and studs is often limited, and variability in the seminal plasma TGFβ content between males is probable, pregnancy outcome is likely to benefit from exogenous administration of TGFβ in many livestock species. TGFβ could be given prior to, or at the initiation of a naturally-sired pregnancy, or at the time of artificial insemination.

DETAILED DESCRIPTION OF THE INVENTION

Materials and Methods

Figure 1:
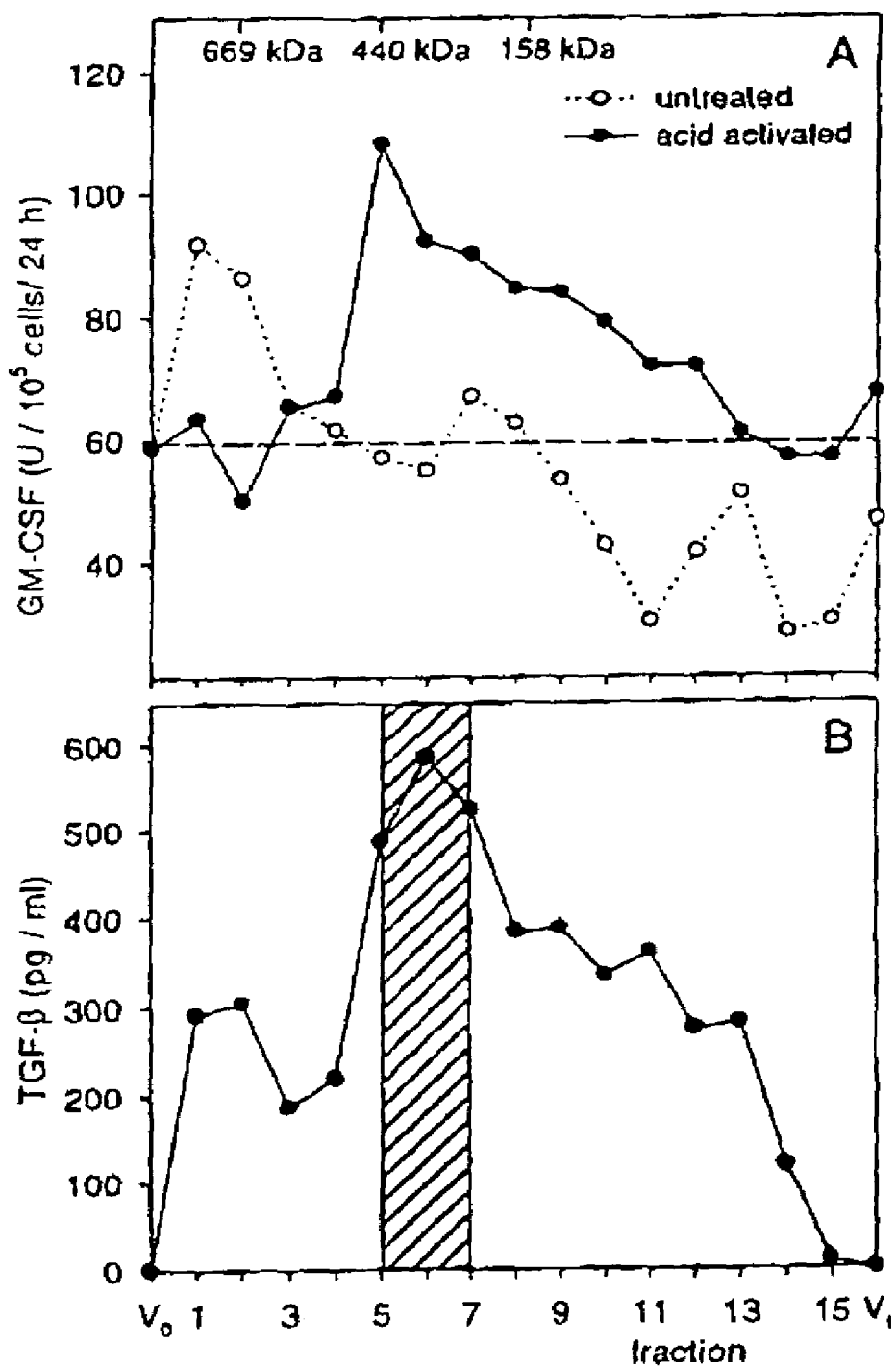
FIG. 1. Sephacryl S-400 size exclusion chromatography of (A) GM-CSF stimulating activity and (B) TGF-β immunoactivity in murine seminal vesicle fluid. In A, uterine epithelial cells from estrous mice were incubated for 16 h with untreated (○, =active TGF-β) or acid activated (●=active+latent TGF-β) fractions of seminal vesicle fluid. After a further 24 h culture, the GM-CSF content of supernatants was determined by FD 5/12 bioassay. Values are means of triplicate cultures and the horizontal dashed line is GM-CSF production by epithelial cells cultured with DMEM-FCS alone. In B, the content of immunoactive TGF-$β_1$ (●) in fractions of seminal vesicle fluid was determined by ELISA. TGF-β bioactivity was detected by Mv-1-Lu cell bioassay. Fractions depicted by the hatched area contained >300 pg/ml, and other fractions contained <50 pg/ml. Data is representative of similar results obtained from three replicate experiments.

Cell Lines, Media, Cytokines and Antibodies.

RPMI-1640 and low glucose Dulbecco's modified Eagle medium (DMEM, GIBCO) were supplemented with 10% fetal calf serum (CSL), 20 mM HEPES pH 7.2, $5\times10^{-5}$ M $\beta$-mercaptoethanol, 2 mM L-glutamine and antibiotics (RPMI-FCS and DMEM-FCS). FD5/12 cells (14), 3T3 fibroblasts, and JR-5 Balb/c fibrosarcoma cells were cultured in RPMI-FCS and mink lung cells [Mv-1-Lu, CCL-64] and uterine epithelial cells were cultured in DMEM-FCS. Human ectocervical cells were cultured in 70% DMEM, 20% Hams F-12 (Gibco), 9% FCS, 1% Neutridoma-SP (Boehringer Mannheim), and 0.4 μg/ml hydrocortisone (Upjohn, Rydalmere, NSW) (ECM-FCS), and human endometrial cells were cultured in DMEM-FCS. Recombinant human (rh)TGF-$\beta_1$ was from R&D Systems, recombinant murine GM-CSF was provided by N. Nicola, The Walter and Eliza Hall Institute for Cancer Research, and recombinant human activin and inhibin were provided by J. Findlay, Prince Henry's Institute for Medical Research. Monoclonal antibodies (mAb) used for immunohistochemistry were anti-CD45 (TIB 122), anti-Mac-1 (CD11b, TIB 128), anti-MHC class II (1a antigen, TIB 120; all from ATCC) F4/80 (15), and RB6-6C5 (16). Mouse anti-bovine TGF-$\beta_{1,2,3}$ mAb (which neutralizes all three mammalian TGF-$\beta$ isoforms) was from Genzyme (Cambridge, Mass.) and chicken anti-bovine TGF-$\beta$1 mAb (neutralizes TGF-$\beta$1, <2% cross reactivity with TGF-$\beta_2$ and -$\beta_3$) was from R & D Systems.

Mice and Surgical Procedures. Adult (8–12 week) female mice of the [Balb/c×C57B1]F1, Balb/c or Balb/k strains, and adult mice of the [CBA×C57B1]F1, CBA, or Balb/c strains were obtained from the University of Adelaide Central Animal House and maintained in a minimal security barrier facility on a 12 hour light/12 hour dark cycle with food and water available ad libitum. Females were synchronised into estrus using the Whitten effect (17) and cycle stage was confirmed by analysis of vaginal smears. For natural mating, females were placed 2 per cage with individual males and the day of sighting of a vaginal plug was nominated as day 1 of pregnancy. Male studs used for collection of accessory gland secretions were all of proven fertility and were rested for one week prior to use.

For intra-uterine injections, uterine horns of estrus females were exteriorised through a dorsal midline excision and injected with 0.2–40 ng rhTGF-$\beta_1$ in 50 ml of RPMI/ 0.1% BSA, or vehicle only, prior to sacrifice of mice 16 hours later for assessment of luminal cytokine content or collection of uterine tissue for immunohistochemistry. Non-surgical administration of sperm/TGF$\beta_1$ to the uterine lumen was achieved by passing a 3 French gauge Tom Cat™ catheter (Sherwood Medical, St. Louis, Mo.) into the uterine lumen (proximal to the point of bifurcation) of restrained females, after visualisation of the cervix with the aid of an auriscope (Heiene, Germany), and manual dilation of the cervix with a fine wire. Each uterine catheter was loaded with 50 μl of sperm/TGF$\beta_1$, which was delivered to the uterine cavity with the aid of a mouth pipette.

Vasectomised mice were prepared by bilateral ligation of the vas deferens through a transverse incision in the abdomen (Hogan et al., 1986), and seminal vesiculectomised mice were prepared by removal of the seminal vesicles through a transverse incision in the abdomen following ligation and severing of the proximal tubule at the base of the gland. The body wall and skin were sutured and the mice were allowed to recover for at least two weeks prior to mating.

All surgical procedures were performed under anaesthesia using Avertin [1 mg/ml tribromomethyl alcohol in tertiary and amyl alcohol (Sigma) diluted to 2.5% v/v in saline: 15 μl/g body weight injected i.p.].

Collection of Reproductive Tract Fluids. Seminal vesicle secretions were extruded from intact glands and solubilised in 6 M guanidine HCl (1:4 v/v), then desalted into DME using 5 ml Sephadex G-25 desalting columns (Pharmacia) before application to epithelial cell cultures. Prostate and coagulating gland secretions were extracted by homogenisation of intact glands in 0.5 ml of PBS/1% BSA, followed by sedimentation of debris at 5000 g. Uterine human fluid was collected 16 h after mating or instillation of rhTGF-β1 into the uterus by flushing each horn with 500 µl of RPMI-FCS. Debris was sedimented at 2000 g and the supernatant stored at −80° C. prior to cytokine assay. In experiments where uterine TGF-β1 was measured, flushings of the right horn were made with 6 M guanidine HCl/0.1% BSA, and desalted into PBS/0.1% BSA prior to cytokine assay. For matings with intact and seminal vesicle deficient males the left horn was flushed with DME to enable confirmation that adequate insemination had occurred (>1×10$^6$ sperm per ml).

Chromatography. Approximately 1 ml of seminal vesicle fluid in 6 M guanidine HCl was applied to a Sephacryl S-400 column (40 cm×16 mm; Pharmacia) equilibrated in 6 M guanidine HCl/0.05 M Hepes pH 7.4. Fractions of 1 ml were collected, desalted into DMEM and assayed for GM-CSF-stimulating activity. Before addition to uterine culture or TGF-β assay half of each fraction was acid activated as previously described (18).

Murine uterine epithelial cell cultures. Uterine epithelial cells were prepared as previously described (19) and plated in 1 ml culture wells (Nunc) at 1–2×10$^5$ cells/ml in 500 µl of DME-FCS. After 4 h incubation at 37° C. in 5% CO2 to allow cell adherence, a further 500 µl of desalted seminal vesicle fluid in DMEM-FCS, cytokines in DMEM-FCS, or DEME-FCS alone, were added. Culture supernatants were collected and replaced with fresh medium at 16 hours, then collected again 24 hours later, at which time adherent cells were quantified as previously described (19). All treatments were performed in duplicate or triplicate.

Human endometrial cultures. Human endometrial cell cultures were prepared under sterile conditions using a modification of the procedure described by Bentin-Ley (64). Briefly, stromal cells were embedded in a collagen matrix, covered by a thin layer of Matrigel (Collaborative Biomedical Products, Bedford, Mass.), which in turn was overlaid with uterine epithelial cells. Uterine epithelial cell supernatants were collected at 12 hrs (basal), replaced with 400 µl of medium containing either rTGFβ$_1$, semen, or fresh culture medium, and supernatants were collected 12 h later. The GM-CSF content of 24 h supernatants were normalised to the GM-CSF content of corresponding 12 h (basal) supernatants.

Human cervical keratinocytes. Human cervical keratinocytes were cultured using a modification of the technique described by Rheninwald and Green (65). Cervical biopsies were obtained from consenting women undergoing hysterectomy for non-malignant gynaecological indications. All women were pre-menopausal, but no distinction was made regarding stage of menstrual cycle at the time of surgery. The cervical biopsies were placed in ice-cold HBSS for transport to the laboratory, washed twice in antibiotic containing medium, and incubated overnight at 4° C. in DMEM containing 5 U dispase (Boehringer Mannheim). Large sheets of keratinocytes were mechanically stripped from the biopsy using sterile forceps after a subsequent 1 h incubation at room temperature. Disaggregation into single cells was facilitated by incubation in DMEM/0.25% trypsin/0.05% collagenase for 30 minutes at 37° C., and repeated aspiration using a needle and syringe. Keratinocytes were cultured in ECM-FCS, at a density of 1–2×10$^5$ cells/ml, over monolayers of murine 3T3 fibroblasts rendered mitogenically inactive by exposure to 4% mitomycin C (Sigma). Keratinocytes were incubated for 5–7 days to enable attachment and displacement of the 3T3 fibroblasts, when the media was replaced with fresh ECM-FCS. Supernatant was collected 12 h later (basal) and replaced with 500 µl of ECM-FCS containing 10 ng of rTGFβ$_1$, 10% semen or culture medium only (control), which in turn was collected 12 hrs later. The GM-CSF content of 24 h supernatants were normalised to the GM-CSF content of corresponding 12 h (basal) supernatants.

Cytokines and Cytokine Assays. GM-CSF was assayed using the GM-CSF dependant cell line FD5/12, essentially as previously described (19). Cell proliferation was determined by the addition of Alamar Blue (Alamar Biosciences) for the last 24 h of the assay or by pulsing with 1 µCi of [$^3$H]-thymidine per well for the last 6 h of the assay. The minimal detectable amount of GM-CSF was 1 U/ml (50 U/ml defined as that producing half maximal FD5/12 proliferation). TGF-β bioactivity was measured using Mv-1-Lu cells as previously described (71), except that cell numbers were quantified by the addition of Alamar Blue for the last 24 h of the assay. The minimal detectable amount of TGF-β in this assay was 15 pg/ml. Cytokine bioassays were standardised against recombinant cytokines and the specificity of the assays was confirmed by the use of cytokine specific neutralising antibodies. TGF-β1 immunoactivity was measured in a specific ELISA (R&D Systems) according to the manufacturers instructions.

Immunohistochemistry. Uterine tissue was embedded in OCT Tissue Tek (Miles Scientific) and frozen in isopropanol cooled by liquid N$_2$, then stored at −80° C. until use. Six µm semi-serial sections were cut from uteri collected at 1400 h on the day of estrus or day 1 of pregnancy, or from mice injected with rhTGF-β1 and fixed in 96% ethanol (4° C./10 min). For mAb staining, sections were incubated with mAbs (neat hybridoma supernatant containing 10% normal mouse serum [NMS]) and goat anti-rat-horseradish peroxidase (HRP; Dako, 1:20 in PBS containing 10% NMS) as detailed previously (19). To visualise HRP or endogenous peroxidase (to detect eosinophils), slides were incubated in diaminobenzidine (Sigma)(5 mg/ml in 0.05 M Tris-HCl pH 7.2) plus 0.02% hydrogen peroxide for 10 min at room temperature. After counterstaining in haematoxylin the secretions were analysed using a video image analysis package (Video Pro, Faulding Imaging, Adelaide) in which the area of positive staining in the endometrial stroma was expressed as a percentage of total cell staining.

Anti-sperm antibody ELISA: A solid phase ELISA technique modified from the protocol of Okada (66) was used to quantify the serum content of sperm-specific immunoglobulins in an isotype-specific manner. Antigen was prepared by disruption of freshly isolated CA sperm (5×10$^6$ sperm/ml in PBS) using a Branson sonicator. 50 µof sperm antigen suspension was added to polystyrene 96 well flat-bottomed ELISA plates (Maxisorb™, Nunc), and incubated overnight at 4° C. Plates were blocked with PBS/3% BSA for 1 h, and stored at −20° C. until use. Serum was diluted 1:4 in PBS, then serially diluted 1:2 to a final dilution of 1:128, before 2 h incubation in the thawed sperm antigen-coated plates. Bound immunoglobulin was detected with rabbit α mouse antibody (Mouse Taylor™, BioRad: 1 hr), followed by biotinylated donkey α rabbit antibody (Amersham, UK; 1:2000 in PBS/1% BSA; 1 hr) and streptavidin-HRP (Amersham; 1:4000 in PBS; 30 mins). HRP was visualised by the addition of tetra methylbenzidine (TMB, Sigma; 20 mins) following acidification of product with 1 M H$_2$SO$_4$. Quantification of each immunoglobulin isotype (IgG, IgG$_{2a}$, IgG$_{2b}$) was performed in duplicate, and all incubations were at room temperature. The antibody titre of each serum was determined by plotting. A$_{450}$ against titration.

Sperm antigen delayed type hypersensitivity (DTH) response: A footpad swelling assay (69) was employed to measure the DTH response against sperm antigens. Balb/c F1 mice were primed on two occasions separated by one month by intra-uterine inoculation with sperm antigens in the presence or absence of TGFβ, and 10 days later, footpad thickness was measured using a micrometer gauge (0.01 mm increment)(Mitutoyo, Tokyo, Japan) before and 24 h following injection into the hind footpad of 25 µl of sperm suspension ($1 \times 10^8$ sperm/ml in HBSS). Antigen-specific swelling was calculated by subtracting the thickness of contralateral footpads injected with HBSS.

Figure 2:
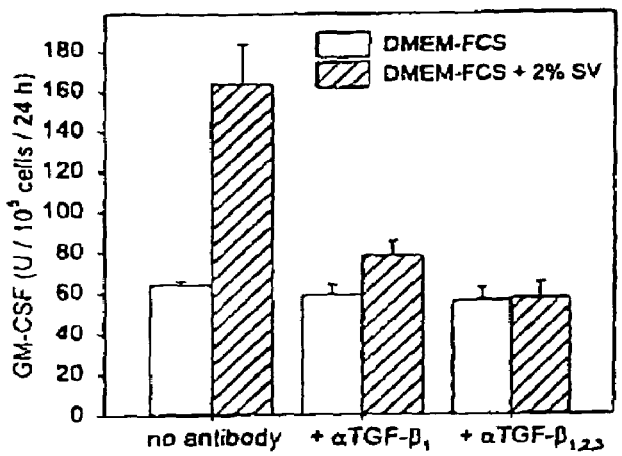
FIG. 2. The effect of neutralising antibodies specific for TGF-$β_{1,2,3}$ and TGF-$β_1$ on GM-CSF stimulating activity in murine seminal vesicle fluid. Uterine epithelia cells from estrous mice were incubated for 16 h with 2% crude seminal vesicle fluid or DMEM-FCS alone, in the presence or absence of mouse anti-bovine TGF-$β_{1,2,3}$ (20 µg/ml) or chicken anti-bovine TGF-$β_1$ (10 µg/ml). After a further 24 h culture, the GM-CSF content of supernatants was determined by FD 5/12 bioassay. Values are mean±SD of triplicate cultures. Data is representative of similar results obtained from three replicate experiments.

Human leukocyte chemotaxis assay. Leukocyte populations were obtained from human peripheral blood using Ficoll-Plaque™ density gradient centrifugation, according to the method described by Boyum (68). Peripheral blood mononuclear cells (PBMC: lymphocytes and monocytes) were suspended in HBSS containing 10% ECM-FCS at $5 \times 10^5$ cells/ml. The chemotaxis assay was a modification of a Boyden chamber protocol described by Bignold (69). Cervicalkeratinocyte culture supernatants (diluted 1:1 with HBSS/10% ECM-FCS), HBSS/10% ECM-FCS, or N-formyl-methionyl-leucyl-phenylalanine (FMLP, Sigma) were added to the bottom half of chambers and were separated from PBMCs by 3 µm polycarbonate mounted adjacent to an 8 µm polycarbonate sparse-pore filter (Nucleopore). Following 45–60 mins incubated at 37° C., during which time PBMCs migrtating through the 8µ filter sparse-pore filter were trapped on the surface of the underlying 3 µm filter, cells were fixed by addition of 1 mol of 10% formalin and quantified by manual counting after staining with Mayer's haemotoxylin. Mean cell numbers (±s.d.) Of triplicate measurements were made for each test sample.

between 150–440 kDA (10.62). The latter moiety was identified as $TGF\beta_1$, on the basis of findings that its GM-CSF stimulating activity was enhanced by acid activation, that $TGF\beta_1$, immunoactivity and bioactivity co-eluted in the same fraction, and that anti-$TGF\beta_1$, neutralizing antibody could block the GM-CSF stimulating activity of this fraction (FIGS. 1,2). The molecular weight of GM-CSF stimulating activity in seminal vesicle fluid (150–440 kDa) is consistent with that of the latent form of $TGF\beta_1$, a complex of 230–290 kDa which comprises the mature TGF-β dimer (25 kDa) non-covalently associated with a 75–80 kDa latency associated protein and a 130–190 kDa binding protein (23).

Figure 3:
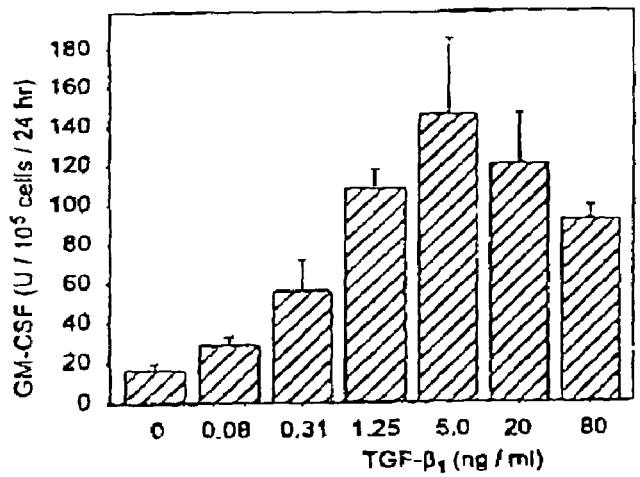
FIG. 3. The effect of TGF-$β_1$ on GM-CSF production by uterine epithelial cells in vitro. Uterine epithelial cells from estrous mice were incubated for 16 h with 0.08–80 ng/ml recombinant human TGF-$β_1$. After a further 24 h culture, the GM-CSF content of supernatants was determined by FD 5/12 bioassay. The mean±SD of triplicate wells is shown. Data is representative of similar results obtained from four replicate experiments.
Figure 4:
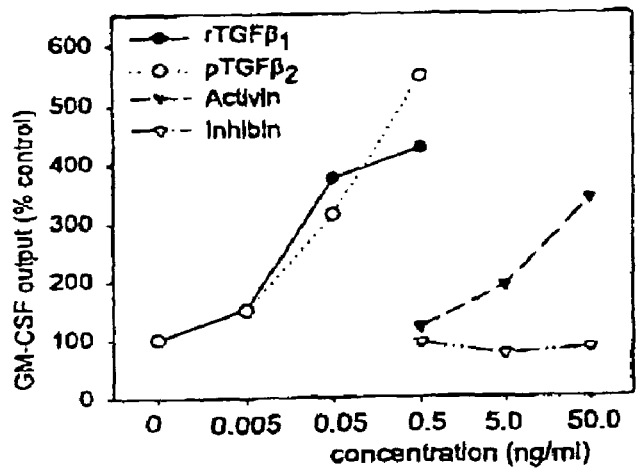
FIG. 4. The effect of TGF-$β_2$, activin and inhibition on GM-CSF production by uterine epithelial cells in vitro. Uterine epithelial cells from estrous mice were incubated for 16 h with 0.05–50 ng/ml recombinant human TGF-$β_1$, porcine TGF$β_2$, or human recombinant activin and inhibin. After a further 24 h culture, the GM-CSF content of supernatants was determined by FD 5/12 bioassay. The mean±SD of triplicate wells is shown. Data is represented of similar results obtained from two replicate experiments.
Figure 5:
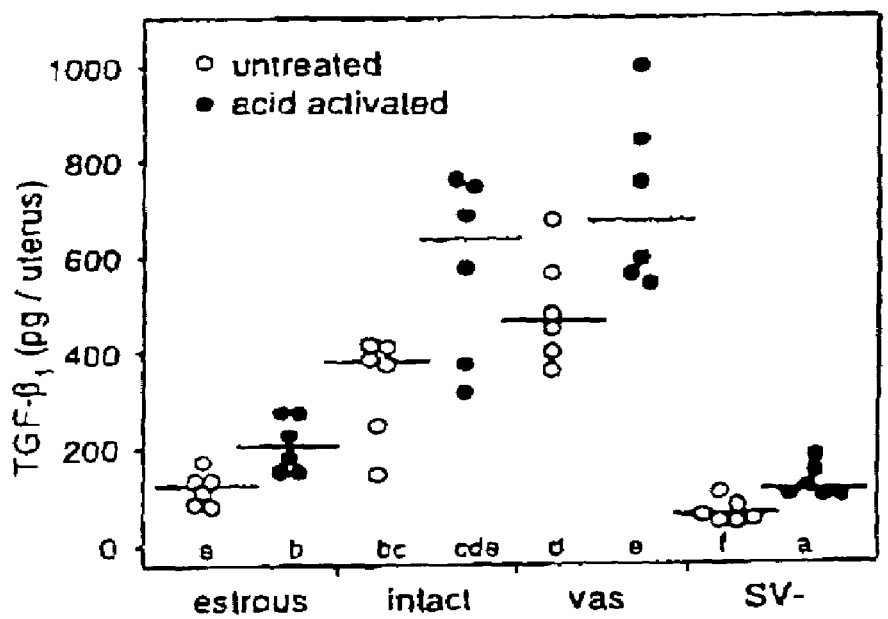
FIG. 5. The effect of seminal composition on the TGF-$\beta_1$ content of uterine luminal fluid after mating. TGF-$\beta_1$ immunoactivity was determined by ELISA in untreated (○=active TGF-$\beta$) or acid activated (●=active+latent TGF-$\beta$) uterine luminal fluids collected from estrous mice, or from mice 1 h after mating with intact, vasectomized (vas) or seminal vesicle deficient (SV−) males. Symbols represent data from individual mice and median values for treatment groups are scored. Data were compared by Kruskal-Wallis one way ANOVA and Mann Whitney Rank Sum test. Data sets labelled on the x-axis with different lower case letters denote statistical significance between treatment groups ($p<0.01$).

The TGF-β1 content of murine seminal vesicle secretions, like that of human seminal plasma (22), was found to be extraordinarily high and second only to that reported for platelet distillate (23). Furthermore the seminal vesicle gland secretions were identified as contributing in excess of 90% of total ejaculate $TGF\beta_1$ content, with the prostate and coagulating gland secretions containing only small amounts of $TGF\beta_1$. The addition of $rTGF\beta_1$ to uterine epithelial cells in culture and in vivo was confirmed to increase uterine epithelial GM-CSF output in a dose responsive manner (FIG. 3).

Figure 6:
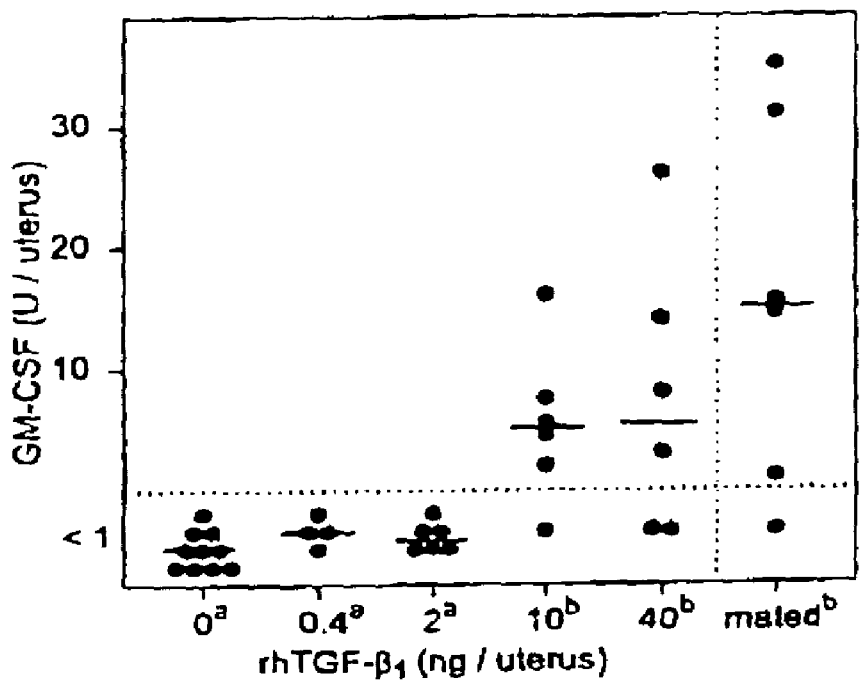
FIG. 6. The effect of intra-uterine TGF-$\beta_1$ on the GM-CSF content of uterine luminal fluid. Fluids were collected 16 h after natural mating with intact males, or after administration of 0.4–40 ng recombinant human TGF-$\beta_1$ in 50 μl PBS/1% BSA, or vehicle only, to the uterine luminal cavity of estrous mice. Symbols represent data from individual mice and median values for treatment groups are scored. Data were compared by Kruskal-Wallis one way ANOVA and Mann Whitney Rank Sum test. Data sets labelled on the x-axis with different lower case letters denote statistical significance between treatment groups ($p<0.01$).

The administration of rTGFβ1 to the uterine lumen of oestrus mice was observed to not only increase uterine GM-CSF production, but also initiate an influx and activation of inflammatory cells similar to that seen following mating (Table 1 and FIG. 6). This result further supports the proposal that TGFβ can fully replicate the post-mating inflammatory response induced in the natural situation by seminal plasma.

Figure 7:
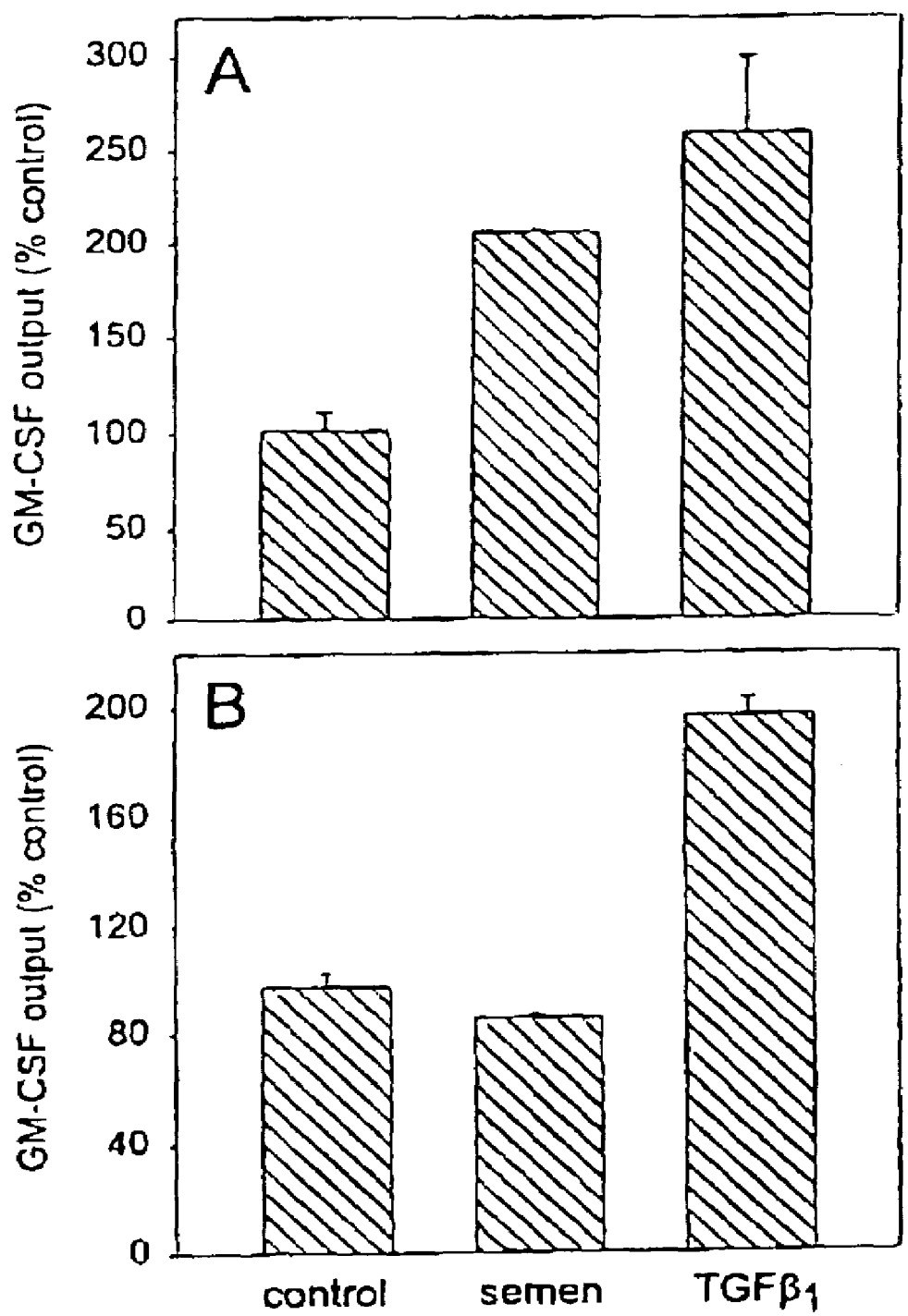
FIG. 7. The effect of rTGF$\beta_1$ and semen on GM-CSF output from human reproductive tract epithelial cells. The GM-CSF content of culture supernatant collected from (A) cervical keratinocytes and (B) endometrial cell cultures was determined by commercial ELISA. 12 hours after the addition of dilute whole semen (10% vol/vol) or 10 ng/ml rTGF$\beta_1$.

In vitro experiments with human cervical keratinocytes and endometrial tissue indicated that both semen and $rTGF\beta_1$ can elicit an increase in GM-CSF production from reproductive tract tissues in women (FIG. 7). Furthermore, the content of leukocyte chemotactic activity in supernatants from keratinocyte cultures was enhanced by treatment with either semen or $rTGF\beta_1$ (FIG. 8), further supporting a principal role for seminal TGFβ in the post-mating inflammatory cascade in women (63).

TABLE 1

The effect of intra-uterine injection with TGF-β₁ on endometrial leukocyte parameters.

| treatment | a | CD45 | F4/80 | Mac-1 | Ia | RB6-8C5 | peroxidase |
|---|---|---|---|---|---|---|---|
| vehicle | 5 | 15 (8–9)ᵃ | 15 (15–25)ᵃ | 9 (7–21)ᵃ | 20 (8–23)ᵃ | 11 (5–15)ᵃ | 4 (4–7)ᵃ |
| rhTGF-β₁ | 4 | 28 (13–39)ᵃᵇ | 37 (30–48)ᵇ | 23 (18–42)ᵃ | 25 (15–25)ᵃᵇ | 15 (4–20)ᵃ | 15 (11–19)ᵇ |
| mated | 4 | 41 (30–60)ᵇ | 31 (21–49)ᵇ | 48 (46–56)ᵇ | 32 (26–57)ᵇ | 36 (15–41)ᵇ | 13 (10–20)ᵇ |

EXAMPLE 1

Seminal TGFβ Initiates the Post Mating Inflammatory Response in Mice and Humans The cytokines GM-CSF, produced by the uterine epithelium following contact with seminal vesicle secretions, is through to be pivotal to the generation of material tolerance since it is largely responsible for initiating the leukocyte influx into the female reproductive tract after mating and for increasing the antigen presenting capacity of these cells.

Seminal vesicle fluid was fractionated by size exclusion chromatography in order to identify GM-CSF-stimulating activity. Two fractions were identified; a high molecular weight (650 kDA) proteinaceous moiety and a intermediate molecular weight, more heterogenous moiety eluting Tissues were collected 16 h after natural mating with intact males, or after administration of 20 ng $rhTGF-\beta_1$ in 50 µl PBS/1% BSA, or vehicle only, to the uterine luminal cavity of estrous mice. The reactivity of endometrial tissue with mAbs specific for all leukocytes (anti-LCA), macrophages (F4/80 and anti-Mac-1), neutrophils (anti-Mac-1 and RB6-8C5), and activated macrophages/dendritic cells (Ia), was determined by immunohistochemistry and video image analysis. Eosinophils were detected by staining for endogenous peroxidase activity (peroxidase). Reactivity with mAbs are expressed as the median (range) percent positivity. The number of mice in each experimental group=n. Data were compared by Kruskal-Wallis one way ANOVA and Mann Whitney Rank Sum test. Data sets labelled with different lower case letters within columns denote statistical significance between treatment groups (p<0.01).

EXAMPLE 2

Seminal Vesicle Fluid Modulates Maternal Reproductive Performance and the Maternal Immune Response to Paternal Antigens Previously, exposure to semen at mating was found to cause an intense but transient inflammatory response, and factors in seminal plasma derived from the seminal vescile were implicated in this response. In studies in mice, the inventors have identified seminal vesicle fluid as a pivotal determinant in optimal embryo development and implantation. Furthermore, exposure to semen at mating has been shown to have an important role in inducing maternal tolerance prior to implantation, and factors present in seminal plasma have been identified as necessary for induction of this state, suggesting that the beneficial effect of seminal plasma on pregnancy outcome may at least in part be due to the immune deviating effects of this fluid.

To test the importance of exposure to seminal vesicle fluid for pregnancy success, Balb/c F1 females were mated with CBA males from which the seminal vesicles had been surgically removed (SV-studs). No implantation sites were present in the uterus on day 17 of pregnancy (n=12 females). This total infertility was not due to a lack of fertilization, but rather was associated with implantation failure or early fetal resorption. This may reflect insufficient material tolerance of the semi-allogeneic embryos due to the lack or exposure to seminal vesicle fluid TGFβ at mating.

TABLE II

Effect of seminal plasma on embryonic development of mice.

|  | Intact | SV- |
|---|---|---|
| Number of females with embryos on day 3 (%) | 8/8 (100%) | 8/8 (100%) |
| # embryos @ day 3 (mean ± SD) | 8.0 ± 2.1 | 9.0 ± 2.0 |
| Number of females with implantation sites on day 17 (%) | 10/10 (100%) | 0/12 (0%) |
| # implants @ day 17 (mean ± SD) | 7.5 ± 1.8 | 0 |

Balb/c F1 mice were mated naturally with intact or seminal vesicle-deficient (SV-) CBA males were sacrificed at 1600 h on day 3 to assess embryonic development, or on day 17 to determine number of implantation sites.

To investigate the importance of semen, particularly seminal vesicle fluid, on the induction of Th1 immune response to paternal MHC antigens, Balb/k (H-$2^k$) female mice were mated with intact Balb/k or congenic Balb/c (H-$2^d$) stud males, or Balb/c SV- studs. To achieve pseudopregnancy, the uteri of Balb/k females were ligated at the oviductal junction 2 weeks prior to mating. Immune responsiveness of MHC class I (H-$2^d$) antigen was assessed by measuring the growth of tumor cells injected on day 4 of pregnancy of pseudopregnancy. Tumor cells were rejected in most Balb/k females mated with Balb/k males, but grew in pregnant or pseudopregnant Balb/k females mated with Balb/c males. In contrast, tumors did not usually grow in Balb/k mice mated with SV- Balb/c males. These data demonstrates that exposure to semen is sufficient to induce specific tolerance to paternal MHC class I antigens, even in the absence of an ensuring pregnancy, and show that this tolerance is dependant on factors derived from the seminal vesicle (Table III).

TABLE III

Effect of pregnancy and psuedopregnancy on rejection of Balb/c JR-5 fibrosarcoma cells in Balb/k mice.

| Female | Male | status at JR-5 injection | tumor growth at day 17 (%) | median tumor size # |
|---|---|---|---|---|
| Balb/c |  | virgin | 11/11 (100) | ++++ |
| Balb/c | Balb/c | d4 pregnant | 5/5 (100) | ++++ |
| Balb/k |  | virgin | 0/10 (0) | − |
| Balb/k | Balb/c | d4 pregnant | 13/14 (93) | +++ |
| Balb/k | Balb/c (vas) | d4 psuedopregnant | 5/7 (71) | ++ |
| Balb/k | Balb/c (SV-) | d4 pregnant | 4/11 (36) | ++ |
| Balb/k (ut lig) | Balb/c | d4 psuedopregnant | 9/9 (100) | +++ |
| Balb/k | Balb/k | d4 pregnant | 5/15 (33) | + |
| Balb/k | C57Blk × CBA | d4 pregnant | 4/8 (50) | + |
| Balb/k (ut lig) | C57Blk × CBA | d4 psuedopregnant | 4/8 (50) | + |

Balb/c (H-2d) or Balb/k (H-2k) female mice were mated with Balb/c or C57Blk×CBA F1 (H-2b/k) studs. In some groups the uteri of Balb/k females were ligated at the oviductal junction 2 weeks prior to mating (ut lig). Other groups of intact Balb/k mice were mated with vasectomised Balb/c males (vas) or Balb/c males from which the seminal vesicles were removed at least 2 weeks prior to mating (SV-). The day of finding a vaginal plug was designated day 1 of pregnancy or pseudopregnancy. Balb/c tumor cells (JR-5 fibrosarcoma cells, $10^5$) were injected s.c. on day 4, and tumor growth (diameter, in two dimensions) was measured on day 17 of pregnancy or pseudopregnancy (++++ =>8 mm; +++=>5 mm; +=1–3 mm).

EXAMPLE 3

Figure 8:
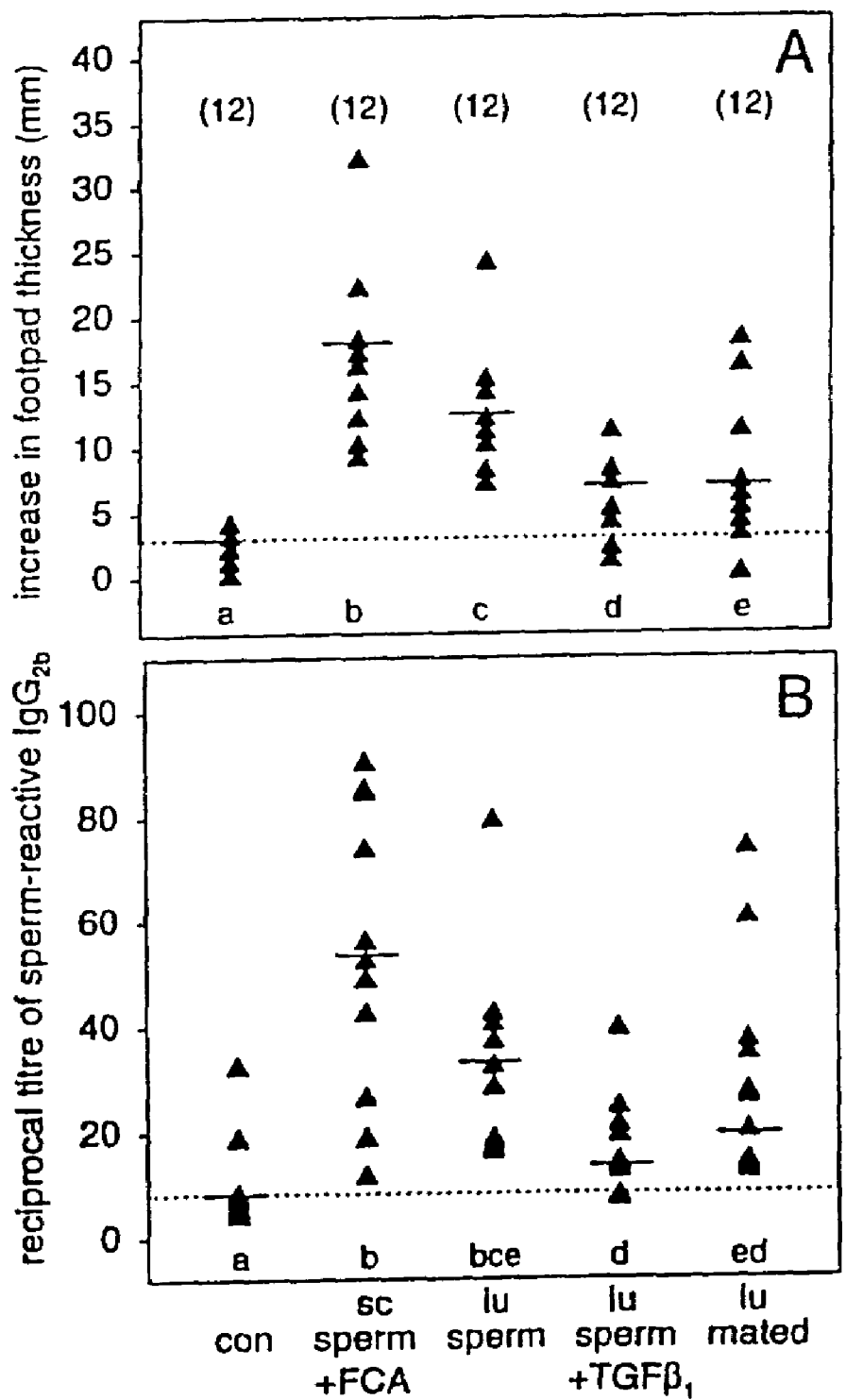
FIG. 8. The effect of intra-uterine priming with sperm and TGF$\beta$ on induction of Th1-type immunity. Balb/c F1 female mice were immunised by intra-uterine infusion with CBA sperm in the presence or absence of 10 ng rTGF$\beta$. Additional groups of uterine-ligated mice were mated naturally with CBA males, or were given sub-cutaneous immunisations with sperm in complete Freund's adjuvant. Ten days later mice were assessed for DTH to sperm antigens, or serum content of anti-sperm IgG2b immunoglobulin. Data was compared by Kruskal-Wallis one way ANOVA, followed by Mann Whitney rank sum test with different superscripts indicating significant differences ($p<0.05$).

Seminal TGFβ is an Immune Deviating Agent to assess the effect of TGFβ on induction of Th1 and Th2 immune responses against CBA sperm antigens, Balb/c F1 female mice were immunised by intra-uterine infusion with CBA sperm, in the presence or absence of rTGFβ, on two occasions separated by 4 weeks. Development of Th1 anti-sperm immunity was assessed two weeks later by measuring the DTH response to a subcutaneous sperm antigen challenge, and by measuring serum content of anti-sperm reactive immunoglobulin of the $IgG_{2b}$ subclass. Whereas sperm administered alone or in the presence of Freunds Complete Adjuvant elicited a strong DTH response and a moderate IgG2b antibody response, immunisation in the presence of TGFβ substantially diminished both of these parameters, and was comparable to the response elicited by natural mating (FIG. 8). In contrast, synthesis of sperm-reactive immunoglobulin of the IgG1 isotype (indicating induction of a Th2 response) occurred to a similar extent in all treatment groups, regardless of the presence of TGFβ in the immunising inoculum.

In another experiment, the effect of TGFβ on the induction of 'tolerance' to paternal MHC antigens associated with sperm was investigated. Balb/k (H-2k) female mice that were given intra-uterine infusions of sperm from Balb/c (H-2d) males together with rTGFβ$_1$ were not able to reject paternal MHC antigen-bearing tumour cells injected 4 days later, where tumours were rejected in naive mice or mice given sperm alone (Table IV). Tumour rejection was also compromised in mice that administered TGFβ without sperm antigen, although tumours in this treatment group were not as large as those which grows in mice that received both antigen and TGFβ.

Both of these experiments show that delivery of paternal antigens in combination with TGFβ to the female reproductive tract can generate systemic paternal antigen-specific tolerance, specifically by inhibiting the Th1 compartment of the immune response. This immune deviating effect is dependent on the administration of TGFβ since antigen given alone elicits Th1 immunity as opposed to tolerance. TGFβ given in the absence of antigen may confer a state of partial, non-antigen specific tolerance.

TABLE IV

The effect of intra-uterine immunisation with Balb/c sperm and TGFβ on rejection of Balb/c JR-5 fibrosarcoma cells in virgin Balb/k mice.

| Treatment | tumor growth at day 17 (%) | median tumor size # |
|---|---|---|
| 5 × 10$^6$ Balb/c sperm | 3/8 (38) | + |
| 10 ng TGFβ | 5/7 (71) | +++ |
| 5 × 10$^6$ Balb/c sperm + 10 ng TGFβ | 6/9 (67) | ++++ |
| Control (PBS) | 0/6 (0) | − |

Balb/k female mice were uterine ligated, and after two weeks rest were synchronised into estrous by administration of GnRH agonist. At 0900 h–1200 h on the day of estrous, mice were anaesthetised and given intra-uterine injections of 5×10$^6$ Balb/c sperm and/or 10 ng TGFβ in 100 ul of PBS (50 ul administered per horn). Balb/c tumor cells (JR-5 fibrosarcoma cells, 10$^5$) were injected s.c. 72 h after surgery, and tumor growth (diameter, in two dimensions) was measured 13 days later (++++=>8 mm; +++=>5 mm; +=1–3 mm).

EXAMPLE 4

Paternal antigen-specific immune deviation improves reproductive performance

Figure 9:
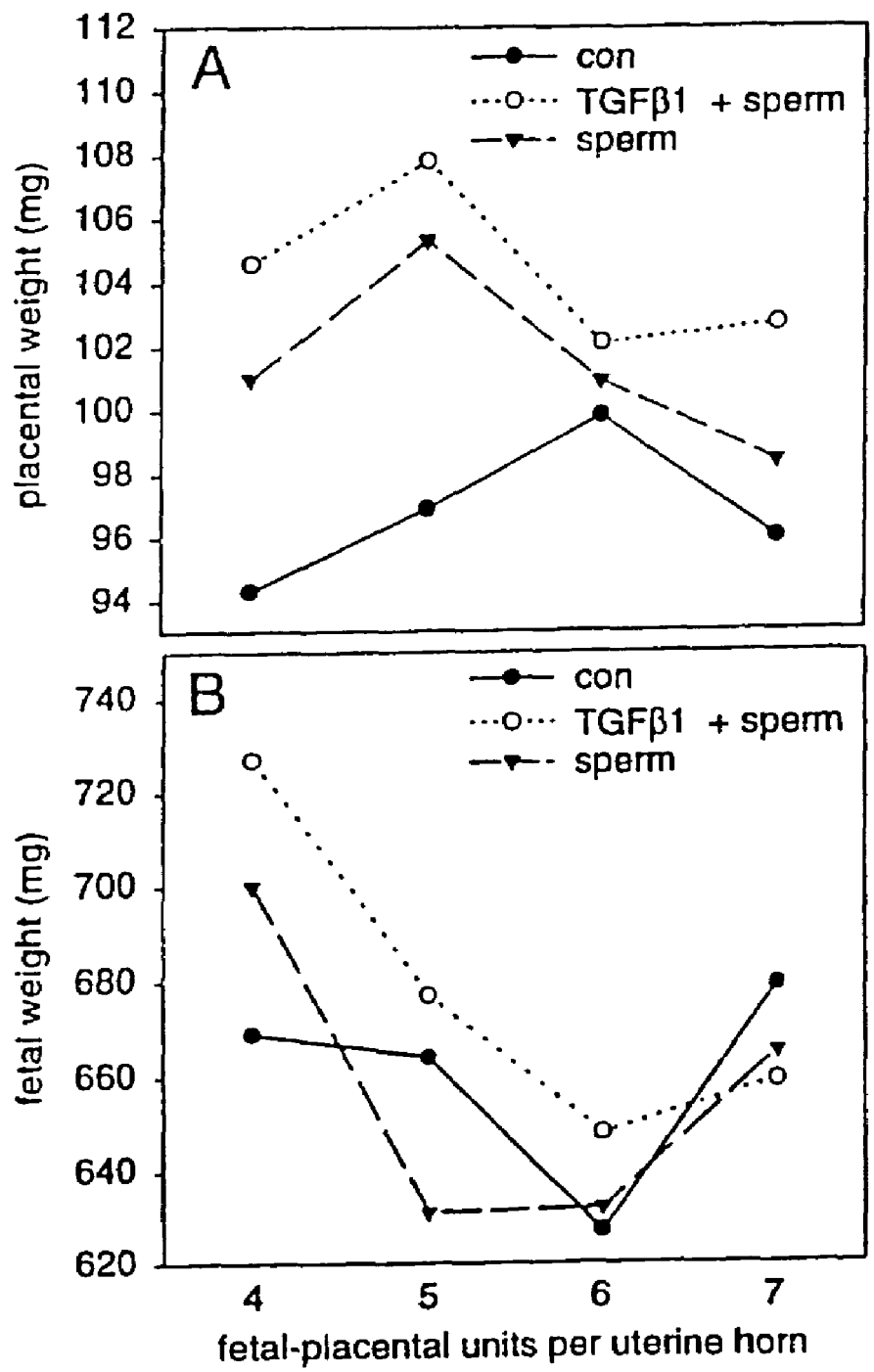
FIG. 9. Effect of prior immunisation with sperm and TGF$\beta$ on fetal and placental weights during subsequent pregnancy in mice. Balb/cF1 female mice were immunised by intra-uterine infusion with CBA sperm in the presence (±TGF$\beta_1$), and were mated naturally with CBA males 2 weeks later. Females were sacrificed on day 17 of pregnancy and fetal (A) and placental weights (B) were determined. Comparisons between groups were made according to the number of viable fetal-placental units per uterine horn, by Kruskal Wallis one-way ANOVA followed by Mann Whitney rank serum test ($p<0.05$).

The experiments described above show that seminal vesicle secretions can elicit Th1 hypo-responsiveness which manifests as 'tolerance' in the maternal immune response specific for seminal antigens, including but not likely to be limited to paternal MHC antigens, deposited in the female reproductive tract at mating. The data suggest that diminished reproductive outcome ensues when a pregnancy has been initiated in the absence of exposure to seminal plasma, perhaps because of inadequate induction of maternal 'tolerance' to conceptus antigens. An experiment was therefor performed to test the hypothesis that a prior state of TGFβ-mediated 'tolerance' to antigens in paternal semen can benefit reproductive performance. This experiment consisted of immunisation by intra-uterine information of Balb/c F1 females with CGA sperm, with or without rTGFβ$_1$, two weeks before mating with intact CBA male studs. Immunisation with sperm plus TGFβ$_1$ resulted in an increase in mean fetal and placental weight (Table V), despite a small decline in litter size which was evident in all females immunised with the sperm regardless of the presence of TGFβ. This increase was still apparent after adjustment for different fetal numbers per uterine horn, thereby discounting an effect of liter size (FIG. 9).

Induction of Th 1 hypo-responsiveness against paternal antigens has been reported to result in an improved pregnancy outcome in women previously experiencing recurrent miscarriage. While no data exist on the ability of paternal antigen/TGFβ immunisation to initiate Th 1 hypo-responsiveness against paternal antigens, or to deviate previously existing Th 1 immune response in women, nor on the ability of TGFβ to improve reproductive outcome, this is likely to be the case. The inventors have been the first to conduct a large randomized, controlled trial investigating the effect of semen exposure on IVF treatment outcome. This trial has confirmed that women exposed to semen (containing paternal antigen and natural TFGβ) around the time of thawed embryo transfer have a reduced risk of early embryonic loss compared to those instructed to abstain (Table VI). This improvement in reproductive outcome is likely to be mediated by material immune tolerance towards paternal antigens initiated by TGFβ and seminal antigens at the time of intercourse.

TABLE V

Effect of prior immunisation with sperm and TGFβ on reproductive outcome in mice

| | Control | sperm + TGFβ$_1$ | sperm |
|---|---|---|---|
| number | 139 | 144 | 103 |
| litter size (total) | 11.4 ± 1.0$^a$ | 10.4 ± 1.2$^b$ | 10.3 ± 0.9$^b$ |
| litter size (viable) | 11.25 ± 1.3$^a$ | 10.1 ± 1.5$^b$ | 10.1 ± 0.9$^b$ |
| # resorptions | 0.167 ± 0.58$^a$ | 0.21 ± 0.58$^a$ | 0.20 ± 0.42$^a$ |
| fetal weight (mg) | 645.2 ± 61.2$^a$ | 677.6 ± 56.6$^b$ | 646.1 ± 49.9$^a$ |
| placental weight (mg) | 97.7 ± 12.3$^a$ | 105.2 ± 12.4$^b$ | 101.8 ± 9.8$^b$ |
| fetal:placental weight ratio | 6.69 ± 0.9$^a$ | 6.5 ± 0.8$^{ab}$ | 6.36 ± 0.8$^b$ |

Balb/F1 female mice were immunised by intra-uterine infusion with SBA sperm in the presence or absence of 10 ng rTGFβ$_1$, and were mated naturally with CBA males 2 weeks later. Females were sacrificed only on day 17 of pregnancy and the number of total, viable and resorbing implantation sites, as well as fetal and placental weights of viable conceptuses, were determined. Values were mean±SD. Comparisons between groups were by Kruska Wallis one-way ANOVA followed by Mann Whitney rank sum test (p<0.05).

TABLE VI

Effect of semen exposure around the time of thawed embryo transfer on early pregnancy outcome.

| | intercourse | abstain | significance |
|---|---|---|---|
| transfer cycles | 59 | 56 | NS |
| embryos transferred | 106 | 107 | NS |
| implantations (%) | 11/106 (10.3) | 11/107 (10.2) | NS |

TABLE VI-continued

Effect of semen exposure around the time of thawed embryo transfer on early pregnancy outcome.

|  | intercourse | abstain | significance |
|---|---|---|---|
| viable conceptus at 6 weeks (%) | 10/106 (9.4) | 7/107 (6.5) | NS |
| transfer cycles with biochemical pregnancy | 9/59* (15.3) | 7/56 (12.5) | NS |
| biochemical pregnancy loss | 0 (0) | 2/11 (8.2) | NS |
| clinical miscarriage | 1/11 (9) | 2/11 (18.2) | NS |
| total pregnancy wastage | 1/11 (9) | 4/11 (36.4) | 0.043 |

Pregnancy outcome following thawed embryo transfer. Patient characteristics were not significantly different between the two groups. A biochemical pregnancy was defined as one serum βHCG exceeding 25 IU and a clinical pregnancy as a conceptus/fetal pole seen at ultrasound at 6 weeks gestation. Statistical analysis was performed using the Chi square calculations. NS=not significant. *=one twin pregnancy.

REFERENCES

1. Barratt et al. (1990) *Hum. Reprod.* 5, 639–648.
2. De et al (1991) *J. Leukocyte Biol.* 50, 252–262.
3. Kachkache et al (1991) *Biol. Reprod.* 45, 860868-868.
4. Mcmaster et al (1992) *J. Immunol.* 148, 1699–1705.
5. Beer & Billingham (1974) *J. Reprod. Fert. Suppl.* 21, 59–88.
6. Clark (1984) in Immunological aspects of reproduction in mammals, ed. Crighton, (Butterworths, London), pp. 153–182.
7. Hunt et al (1984) *Cell. Immunol.* 85, 499–510.
8. Robertson & Seamark (1990) *Reprod. Fertil. Dev.* 2, 359–368.
9. Head et al (1991) in The Molecular and Cellular Immunobiology of the Maternal-Fetal Interface, eds. Wegmann et al (Oxford University Press, New York).
10. Robertson et al. (1996) *J Report Fert* 107, 265–277
11. Robertson et al (1994) in Serono Symposium on the Immunobiology of Reproduction, eds. Hunt & Burnett.
13. Wilbanks et al. (1992) *Eur. J. Immunol.* 22, 165–173.
14. Duhrsen (1988) *Leukemia* 2, 334–342.
15. Austyn & Gordon (1981) *Eur. J. Immunol.* 11, 805
16. Conlan & North, (1994) *J. Exp. Med.* 179, 259–268.
17. Whitten, (1956) *J. Endocrinol.* 14, 160–163.
18. Lawrence et al. (1984) *J. Cell Physiol.* 121, 184–188.
19. Robertson et al. (1992) *Biol Reprod.* 46, 1069–1079.
20. Anderson et al. (1983) *J. Reprod. Fertil.* 68, 1–7.
21. Mann, T. (1964) The biochemistry of semen and the male reproductive tract (John Wiley and Sons, Inc.,
22. Nocera & Chu (1995) *Am. J. Reprod. Immunol.* 33, 282–291.
23. Wakefield et al. (1988) *J. Biol. Chem.* 263, 7646–7654.
24. Massague, (1990) *Annu. Rev. Cell Biol.* 6, 597–641.
25. Andres, (1989) *J. Cell Biol.* 109,. 3137–3145.
26. Wakefield et al (1990) *J. Clin. Invest.* 86, 1976–1984.
27. Wahl (1992) *J. Clin. Immunol.* 12, 61–74.
28. Finlay et al. (1983) *Endocrinology* 112, 856–861.
29. Danglot et al. (1986) *FEBS Lett.* 194, 96–100.
30. Weiner et al (1994) *Annu. Rev. Immunol.* 12, 809–837.
31. Tafuri et al. (1995) *Science* 270, 630–633.
32. Wegmann et al. (1993) *Immunol. Today* 14, 353–356.
34. Anderson & Tarter (1982) *J. Immunol.* 128, 535–539.
35. Lee & Ha (1989) *Int Arch Allergy Appl Immunol* 88, 412–419.
36. Pang et al. (1979) *J. Reprod. Fert.* 56, 129–132.
37. Peitz & Olds Clarke. (1986) *Biol. Reprod.* 35, 608–617.
38. Polge. (1982) in Control of pig reproduction, eds. Cole & Foxcroft. (Butterworths, London), pp. 277–291.
39. Mah et al (1985) *J. Annim. Sci.* 60, 1052–1054.
40. Walker et al. (1992) *Theriogenology* 37, 111–126.
41. Murray et al. (1983) *J Anim Sci* 56, 895–900.
42. Stone et al. (1987) *Proc. Am. Fert. Soc.* 43, 88
43. Klonoff-Cohen et al. (1989) *JAMA.* 262, 3143–3147.
44. Robillard et al (1995) *The Lancet* 344, 973–975.
45. Bellinge et al. (1986) *Fertil. Steril.* 46, 2523–2526.
46. Breyere and Burhoe (1964) *Ann. NY Acad. Sci.* 120, 430–434
47. Kester et al (1971) *J. Clin. Path.* 24, 726–730
48. Dekker et al (1996) Abstract No 516 *Am J Obstet Gyn*
49. Kajina et al *Am J Reprod. Immun.* 17, 91–95
50. Scott et al (1987) *Obst. Gyn.* 70, 645
51. Gleicher (1994) *Am. J Reprod Immun.* 32, 55–72
52. Coulam & Stern Reprod Immun Serono Symposium 97, 205–216, Eds Donero & Johnson
53. Kutten et al (1992) *Mol Androl* 4, 183–193
54. Klonoff-Cohen et al (1989) *JAMA* 262, 3143–3147
55. Robillard et al (1995) *Lancet* 344, 93–975
56. Stephen E H (1996) *Fert Steril* 66, 205–9
57. Hakim et al (1995) *Am J Obstet Gyn* 172, 1510–7
58. Weinberg et al (1988) *Fert Steril* 50, 993–5
59. Lenton et al (1988) *Ann NY Acad Sci* 541, 498–509
60. Neumann et al (1994) *N Eng Med* 331, 239–43
61. Stern et al (1997) *Am J Reprod Immun* 37, 352–3
63. Tremellen et al (1997) *J Reprod Immun* 34, 76–7
64. Bentin-Ley et al (1994) *J Reprod Fert* 101, 327–32
65. Reinwald et al (1975) *Cell* 6, 331–44
66. Okada et al (1993) *Am J Reprod Immunol* 29, 241–6
67. Lee et al. (1989) *Int Arch Allergy Appl Immun* 88, 412–19
68. Boyden SV (1962) *J. Exp Med* 115, 453–61
69. Bignold L P (1989) *J. Immun. Method* 118, 217–25
70. Medawar PB (1953) *Symp Soc Exp Biol* 44, 320–38.
71. Like et al (1986) *J Biol Chem* 261, 13426–29
72. Gordon et al (1987) *Nature,* 326: 403–5
73. Robertson et al. (1991) *The Molecular and Cellular Immunobiology of the Material-Fetal Interface.* (Oxford University Press, New York) pp 191–206. Eds: Wegmann, Nisbett-Brown & Gill.
74. de Moraes & Hansen (1977) *Biol Reprod* 57:106014 1065.
75. Imakawa et al. (1993) *Endocrin.* 132: 1869–71.

The invention claimed is:

1. A method of treating recurrent miscarriage by inducing immune tolerance to a paternal antigen in a mammalian prospective mother lacking said immune tolerance, said method comprising exposing a mucosal surface of said prospective mother to:
    a) semen or an MHC Class I antigen of a prospective father capable of eliciting a Th-1 response; and
    b) substantially purified TGFβ selected from the group consisting of TGFβ1, TGFβ2, and TGFβ3,
    wherein the exposure is at a time and in an amount effective to induce said immune tolerance and is at least one week before attempted conception.

2. A method of treating recurrent miscarriage by inducing immune tolerance to a paternal antigen in a mammalian prospective mother lacking said immune tolerance, said method comprising exposing a muscosal surface of said prospective mother to:

a) semen or an MHC Class I antigen of a prospective father capable of eliciting a Th-1 response; and
   b) a substantially purified TFGβ selected from the group consisting of TGFβ1, TGFβ2, and TGFβ3,
   wherein the exposure is at time and in an amount effective to induce said immune tolerance and is performed over a period spanning at least three months prior to attempted conception.

3. The method according to claim 1 or 2, wherein the prospective mother and father are both human.

4. The method according to claim 1 or 2, wherein the TGFβ and the semen or MHC Class I antigens are administered at one site.

5. The method according to claim 1 or 2, wherein the TGFβ and the semen or MHC Class I antigen are respectively administered at a first site and a different site.

6. The method according to claim 1 or 2, wherein the TGFβ and the semen or MHC Class I antigen are administered temporally spaced apart.

7. The method according to claim 6, wherein the semen or MHC Class I antigen is administered subsequent to an administration of TGFβ.

8. The method according to claim 6, wherein the semen or MHC Class I antigen is administered first followed by administration of TGFβ.

9. The method according to claim 1 or 2, wherein the MHC Class I antigen is from sperm cells of the prospective father.

10. The method according to claim 1 or 2, wherein the semen or MHC Class I antigen is presented in purified or semi-purified form.

11. The method according to claim 10, wherein the purified or semi-purified semen or MHC Class I antigen is presented on an inert or adjuvant carrier.

12. The method according to claim 1 or 2, wherein the TGFβ is supplied in a slow release form.

13. The method according to claim 1 or 2, wherein the exposure of the semen or MHC Class I antigen is to the prospective mother's genital tract in the form of the prospective father's ejaculate.

14. The method according to claim 1 or 2, wherein the mucosal surface is selected from the group comprising of an oral mucosal surface, a respiratory mucosal surface, a gastrointestinal mucosal surface and a genital mucosal surface.

15. The method according to claim 1 or 2, wherein the mucosal surface is a genital mucosal surface.

16. The method according to claim 1 or 2, wherein the mucosal surface is exposed to a concentration of TGFβ of 100 ng/ml.

17. The method according to claim 1 or 2, wherein the mucosal surface is exposed to a concentration of TGFβ of 200 ng/ml.

18. The method according to claim 1 or 2, wherein TGFβ is administered in its active form.

19. The method according to claim 1 or 2, wherein the prospective mother is incapable of converting a sufficient amount of the inactive form of TGFβ to active TGFβ, and the method includes administration of active TGFβ.

20. The method according to claim 1 or 2, wherein the prospective mother is incapable of converting the inactive form of TGFβ to active TGFβ, and the method includes administration of plasmin, so as to increase the level of active TGFβ.

21. The method according to claim 1 or 2, wherein the prospective mother and father are human and the exposure to TGFβ and the semen or MHC Class I antigen of the prospective father is a multiple exposure.

22. The method according to claim 1 or 2, wherein administration of TGFβ and the semen or MHC Class I antigen occurs at least once after attempted conception.

23. The method according to claim 1 or 2, further including a step, prior to exposure to antigens and TGFβ, of diagnosing or testing whether
   (a) the prospective father has adequate levels of TGFβ;
   (b) the prospective mother has the capacity to activate TGFβ, or
   (c) anti-sperm antibodies are present in the prospective mother.

24. The method according to claim 1 or 2, used in conjunction with IVF treatment.

25. The method according to claim 1 or 2 wherein the exposure continues over a period of the first 12 weeks of pregnancy.

26. The method according to claim 1 or 2, wherein the mucosal surface is exposed to a concentration of TGFβ of between 100 and 400 ng/ml.

27. The method according to claim 1 or 2 wherein the mucosal surface is exposed to a concentration of TGFβ of between 100 and 400 ng/mL, with a total of between 100 to 200 ng.

* * * * *